US00PP19564P3

(12) United States Plant Patent
Zampini

(10) Patent No.: US PP19,564 P3
(45) Date of Patent: Dec. 9, 2008

(54) *ORNAMENTAL FLOWERING PLUM TREE NAMED 'CRIPOIZAM'*

(50) Latin Name: *Prunus×cerasifera*
Varietal Denomination: cv. Cripoizam

(76) Inventor: James W. Zampini, c/o Lake County Nursery, Route 84, Box 122, Perry, OH (US) 44081-0122

( * ) Notice: Subject to any disclaimer, the term of this patent is extended or adjusted under 35 U.S.C. 154(b) by 0 days.

(21) Appl. No.: 11/798,024

(22) Filed: May 9, 2007

(65) Prior Publication Data

US 2008/0282433 P1 Nov. 13, 2008

(51) Int. Cl.
*A01H 5/00* (2006.01)

(52) U.S. Cl. ..... Plt./184

(58) Field of Classification Search ..... Plt./184
See application file for complete search history.

*Primary Examiner*—Annette H Para
(74) *Attorney, Agent, or Firm*—Buchanan Ingersoll & Rooney PC

(57) ABSTRACT

A new and distinct variety of *Prunus×cerasifera* plant is provided that was discovered as a seedling of unknown parentage in a cultivated area among trees of the 'Newport' variety (non-patented in the United States). A dense upright columnar growth habit is displayed. The young foliage is copper-red in coloration and at full maturity assumes an attractive deep-purple coloration. Rapid growth is displayed and a larger caliper trunk is formed at an early age. The plant is well suited for providing attractive ornamentation in the landscape.

6 Drawing Sheets

Botanical/commercial classification: *Prunus×cerasifera*/ Ornamental Flowering Plum Tree.
Varietal denomination: cv. Cripoizam.

SUMMARY OF THE INVENTION

The new Plum Tree of the present invention was discovered during 1983 as a seedling of unknown parentage while growing in a cultivated area tended by man. More specifically, the new variety was discovered while growing among trees of the 'Newport' variety of *Prunus×cerasifera* (U.S. Plant Pat. No. 4,987) being grown at Perry, Ohio, U.S.A., in U.S.D.A. Hardiness Zone 6a.

My attention was attracted to the plant of the present invention in view of its distinctive combination of characteristics which differs from that of *Prunus×cerasifera* and all other Plum varieties of which I am aware.

It was found that the new Ornamental Flowering Plum Tree exhibits the following combination of characteristics:

(a) displays a dense upright columnar growth habit, (b) forms distinctly colored leaves, (c) displays in profusion attractive white flowers, (d) displays a rapid growth habit, and (e) forms a larger caliper trunk from an early age.

The emerging foliage exhibits a coppery coloration and at full maturity assumes an attractive deep-purple coloration.

The new variety can be readily distinguished from previously known *Prunus×cerasifera* varieties in view of the recited combination of characteristics. The growth habit is extremely upright and forms a very narrow columnar head. Such growth habit is significantly different than the upright oval growth habit of the 'Newport' variety. Also, the faster growth rate with respect to height and trunk caliper is noteworthy. Unlike the 'Newport' variety which forms small pink flowers, the flowers of the new cultivar are white with prominent reproductive organs. The foliage from the time of its emergence through full maturity provides changing attractive coloration.

The new variety well meets the needs of the horticultural industry and is well suited for growing as attractive distinctive ornamentation in the landscape.

Plants of the new variety have been asexually reproduced at Perry, Ohio, U.S.A., through the use of softwood cuttings and by T-budding or chip budding onto *Prunus×cerasifera myrobala* understock. The characteristics of the new variety have been found to be strictly transmissible by such asexual propagation, and the new cultivar reliably reproduces in a true-to-type manner from one generation to another.

The new variety of the present invention has been named 'Cripoizam', and is being marketed under the CRIMSON POINTE trademark.

BRIEF DESCRIPTION OF THE PHOTOGRAPHS

DETAILED DESCRIPTION

The chart used in the identification of color is the R.H.S. Colour Chart of The Royal Horticultural Society, London, England. Other reference to color is to be accorded its ordinary dictionary significance. The description is based upon the observation of plants of the new variety having an age of approximately 8 years while being grown outdoors at Perry, Ohio, U.S.A.

The original plant of the new variety exhibits extremely columnar growth habit. The branch crotch angles commonly are approximately 5 to 15 degrees with the branches initially curving upwards and becoming substantially parallel to the trunk. It is anticipated that at full maturity, based upon observations to date, the new variety of the present invention will assume a height of approximately 20 feet and a width of approximately 5 to 6 feet at the widest point. The rate of growth of the overall tree including the diameter of the trunk is rapid and exceeds that of the species and previously known Ornamental Plum varieties, such as the 'Newport' variety (U.S. Plant Pat. No. 4,987).

The vegetative parts of the new variety are typical of the genus except as specifically indicated hereafter. The entire, alternate, simple leaves are elliptical in configuration and serrulated at the margins. The apices are acute to pointed with the bases of the leaves being acute to rounded. The mature leaves commonly are approximately 3 to 3½ inches in length (including the petiole) and narrow at the base. The petiole commonly measures approximately ⅜ to ⅝ inch in length.

Figure 1:
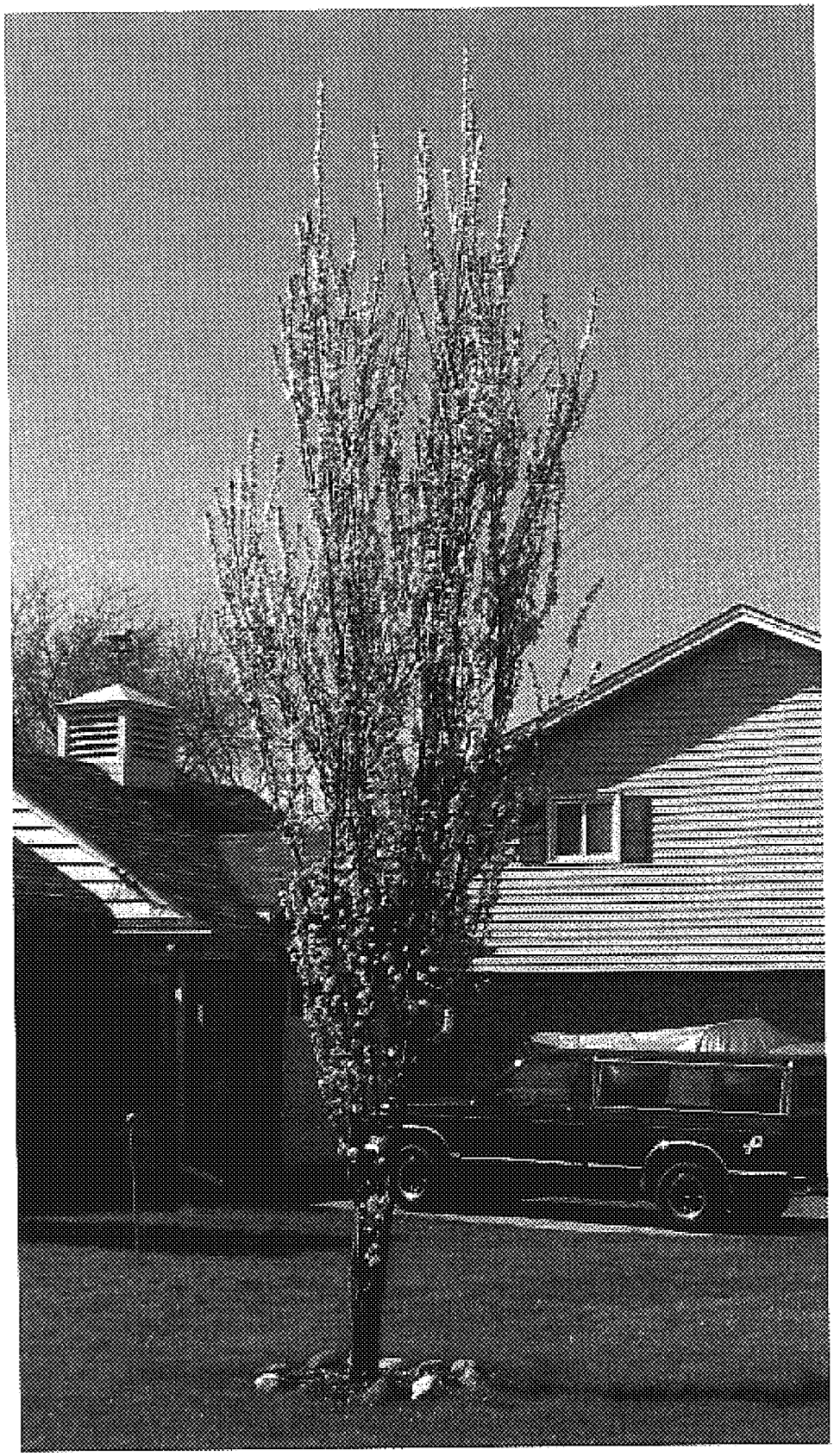
FIG. 1 illustrates a twenty-two-year-old specimen of the new variety while in full flower during the spring when growing in a residential landscape setting.
Figure 2:
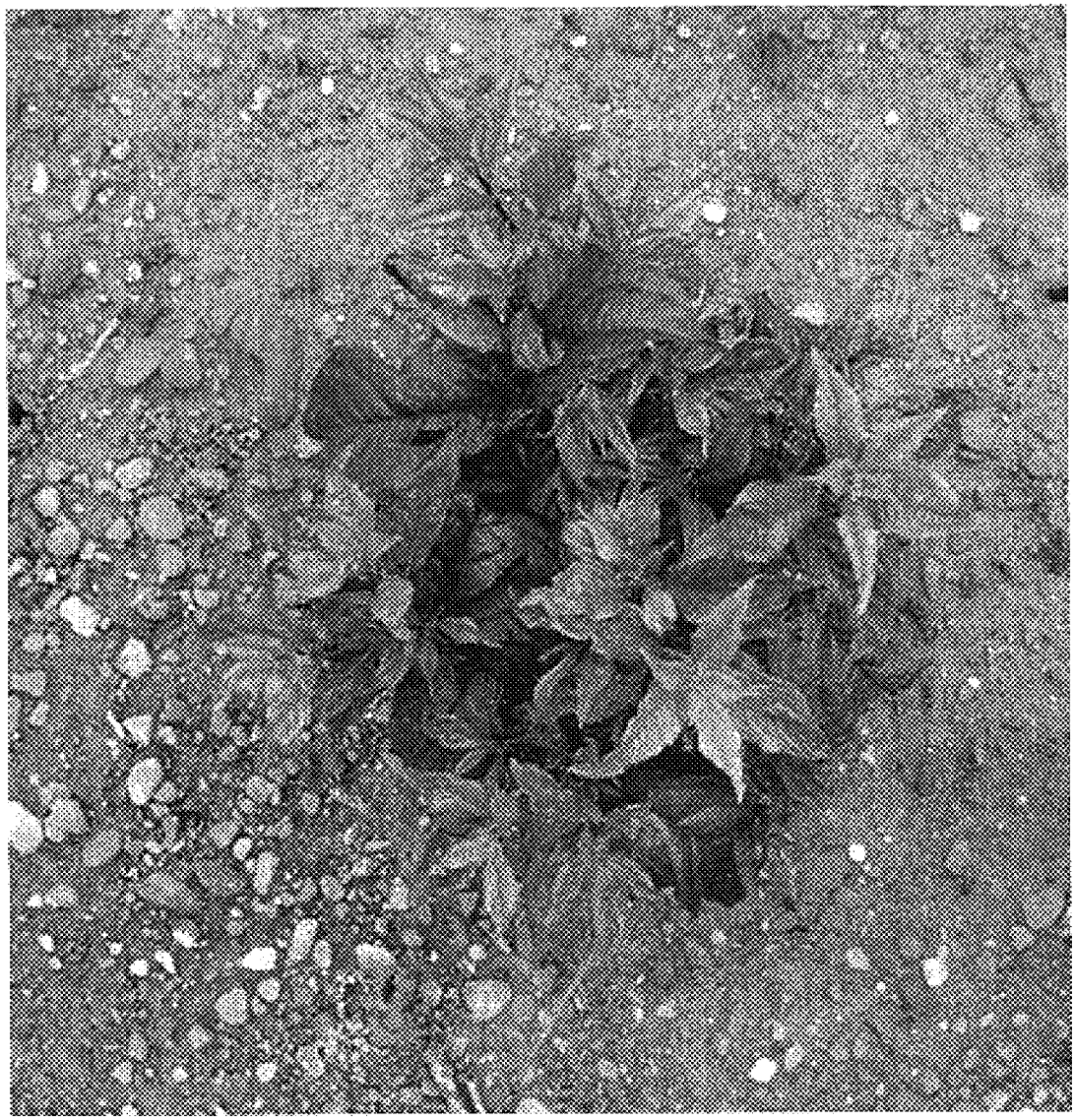
FIG. 2 illustrates a close view of a liner bed specimen of the new variety during late spring. The coppery coloration of the newly formed foliage is shown.

The emerging leaves of the new variety in the spring are of a distinctive copper-red coloration. The leaves of the new variety in the spring on the upper surface as they unfold commonly are initially near Yellow Green Group 153D in coloration and subsequently change in coloration with increasing maturity to Orange-Red Group 35A and 35B. See FIG. 1 in this regard. Next, the coloration of the leaves changes to near Red Group 53B and at full maturity assumes a deep-purple coloration. Such fully mature leaves commonly are near Greyed-Purple Group 187A in coloration on the upper surface and near Red-Purple Group 59A on the under surface.

Immature twigs are near Greyed-Orange Group 176A in coloration. As the branches mature, they commonly are near Grey-Orange Group 177A in coloration. Elongated light-brown to orange lenticels (near Greyed-Orange Group 166C) measuring approximately 1/16 inch in size, commonly are present at a generally typical frequency on immature and mature twigs. The trunk bark commonly is near Brown Group 200B in coloration.

Figure 3:
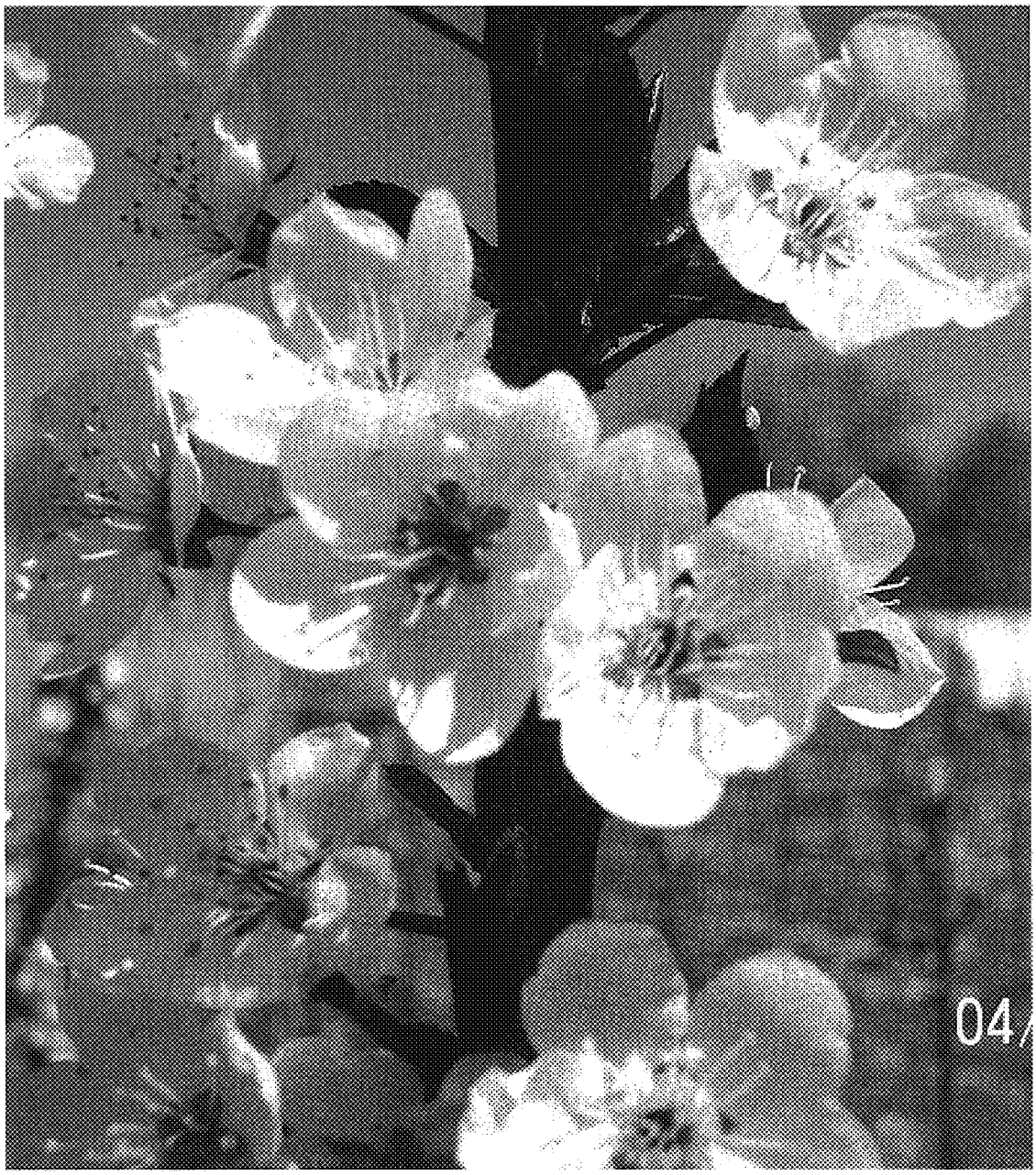
FIG. 3 illustrates a close view in the springtime of fully open flowers of the new variety.
Figure 4:
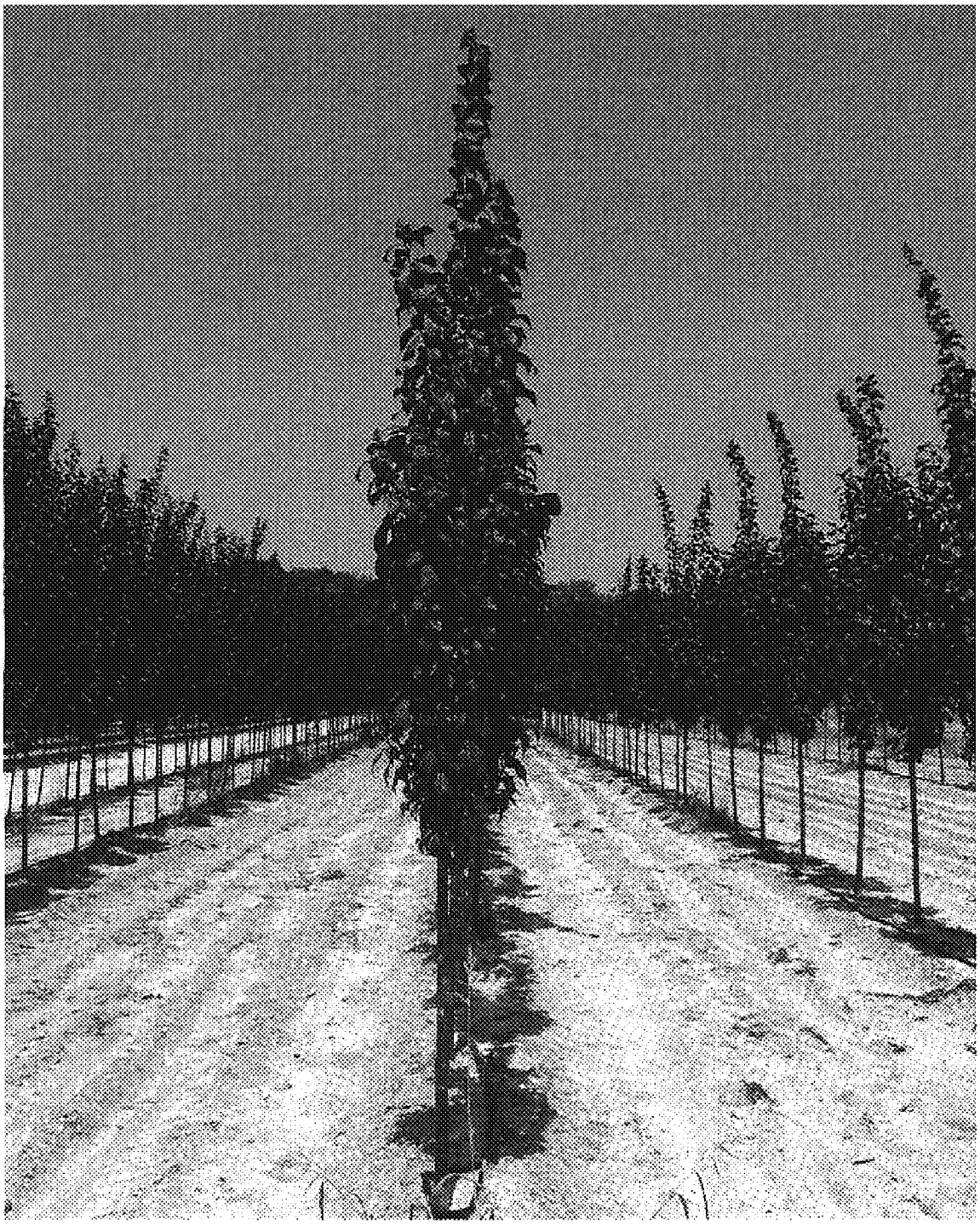
FIG. 4 illustrates rows of field grown four-year-old specimens of the new variety during the summer. The generally uniform columnar growth habit and deep-purple mature foliage coloration are illustrated.
Figure 5:
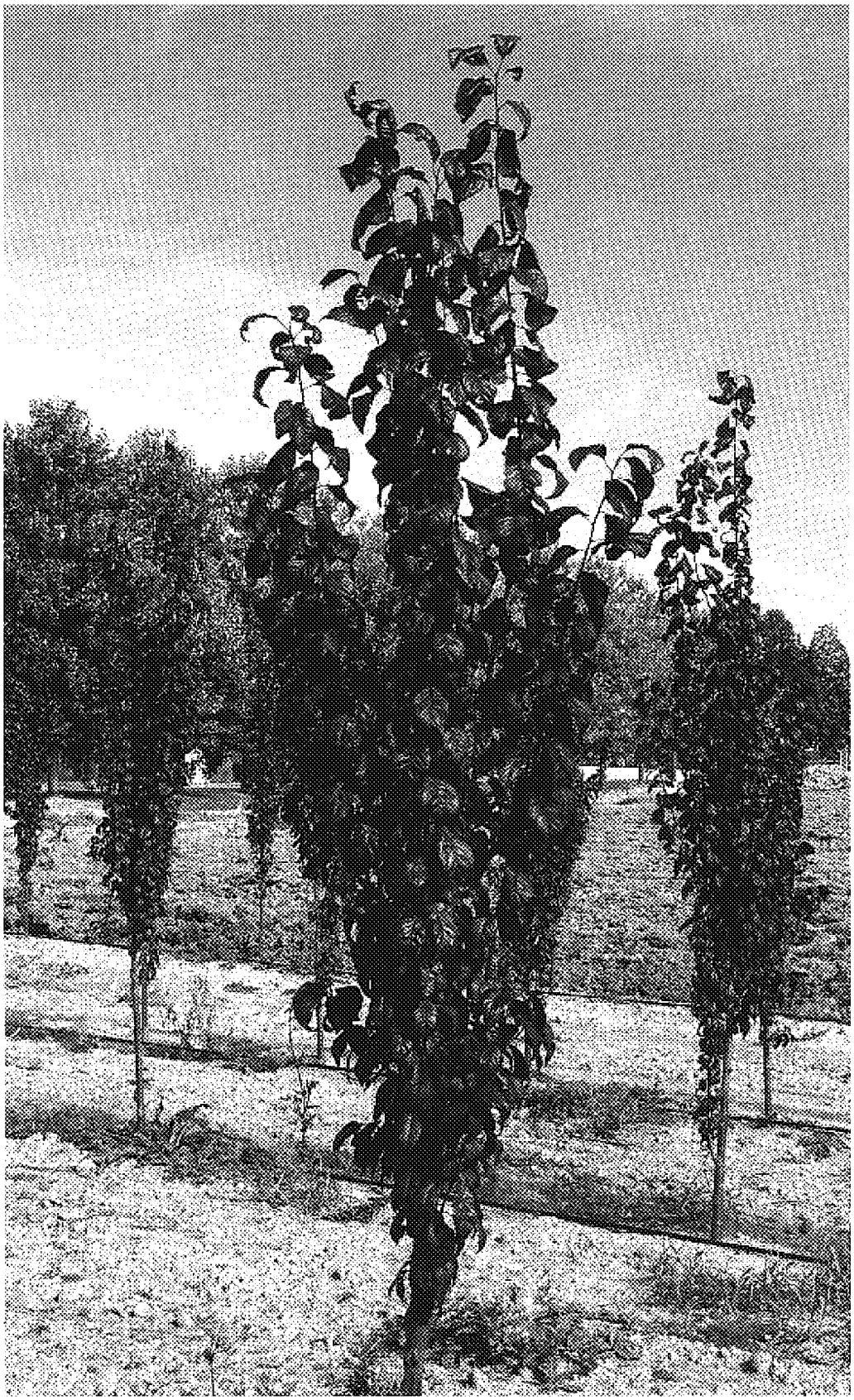
FIG. 5 illustrates a closer view of field grown specimens of the new variety during the summer.

The blossom appearance of the new variety is similar to that of the genus. The new variety forms in profusion attractive white blossoms which generally correspond to the color of White Group 155D with a slight pink appearance at the base. The petal number commonly is 5, and sometimes 6. The flowering commonly begins before leaf break. The overall configuration of the flowers is generally typical of the genus. The flowers are perfect, single and extremely numerous. Blossoming commonly occurs during early April to early May at Perry, Ohio, U.S.A., where it commonly extends over approximately 10 days depending upon the weather conditions that are encountered. The flowers are commonly borne in a solitary manner and are fragrant. As shown in FIG. 3, the blossom petals bear generally rounded apices and somewhat tapered bases. The petal margins sometimes are slightly ruffled and slightly reflexed. The reproductive organs are typical of a *Prunus×cerasifera* angiosperm flowering plant, are illustrated in FIG. 3, and are substantially similar to those of the 'Newport' variety. The filaments are white and the anthers are yellow-orange in coloration.

Figure 6:
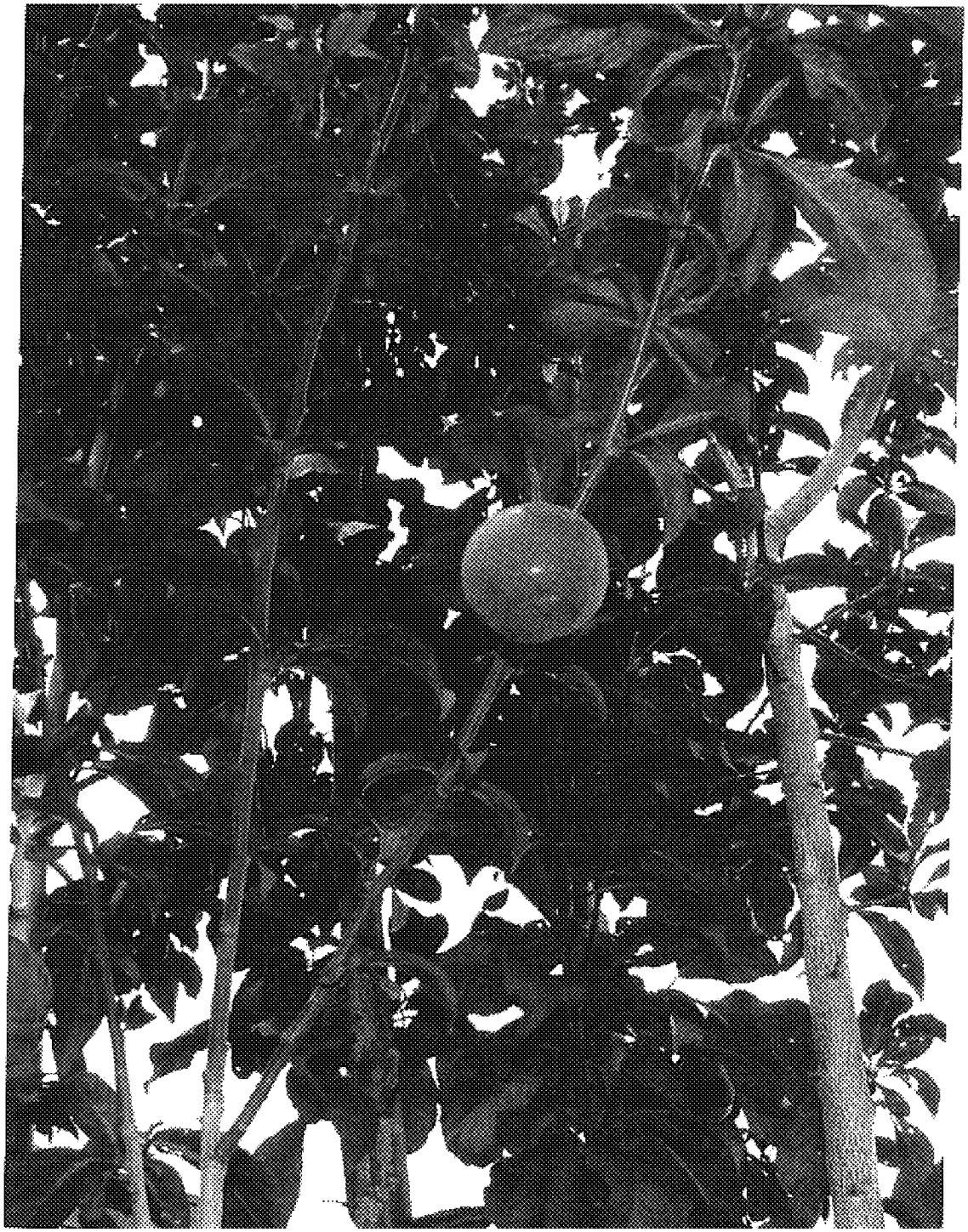
FIG. 6 illustrates a closer view of the mature foliage as well as a representative fruit specimen of the new variety. Such fruit is only sparsely formed.

During observations to date, fruit has been formed in only a sparse quantity and is not considered to be ornamental in nature. See FIG. 6 in this regard. Typical of the species, the fruit is a reddish drupe approximately 1 inch in diameter.

When grown at Perry, Ohio, U.S.A., the new variety has exhibited disease resistance under observations to date and has not been affected to any degree by common *Prunus* diseases or by insects which commonly attack *Prunus*. The new variety has proven to be hardy when tested in U.S.D.A. Hardiness Zone 4.

Plants of the new 'Cripoizam' variety have not been observed under all possible environmental conditions to date. Accordingly, it is possible that the phenotypic expression may vary somewhat with changes in light intensity and duration, cultural practices, and other environmental conditions.

I claim:

1. A new and distinct Ornamental Flowering Plum Tree having the following combination of characteristics:

(a) displays a dense upright columnar growth habit, (b) forms distinctly colored leaves, (c) displays in profusion attractive white flowers, (d) displays a rapid growth habit, and (e) forms a larger caliper trunk from an early age;

substantially as illustrated and described.

* * * * *